US00PP19019P2

(12) United States Plant Patent
Miedema-Jorna

(10) Patent No.: US PP19,019 P2
(45) Date of Patent: Jul. 15, 2008

(54) ***PETUNIA* PLANT NAMED 'FORT SALMON 2004'**

(50) Latin Name: *Petunia×hybrida*
Varietal Denomination: Fort Salmon 2004

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/728,151

(22) Filed: Mar. 23, 2007

(51) Int. Cl.
*A01H 5/00* (2006.01)

(52) U.S. Cl. ..... Plt./356
(58) Field of Classification Search ..... Plt./356
See application file for complete search history.

*Primary Examiner*—Annette H Para
(74) *Attorney, Agent, or Firm*—C. A. Whealy

(57) ABSTRACT

A new and distinct cultivar of *Petunia* plant named 'Fort Salmon 2004', characterized by its upright to outwardly spreading growth habit; freely branching habit; freely flowering habit; large salmon pink-colored flowers; and good garden performance.

1 Drawing Sheet

Botanical designation: *Petunia×hybrida.*
Cultivar denomination: 'Fort Salmon 2004'.

BACKGROUND OF THE INVENTION

The present invention relates to a new and distinct cultivar of *Petunia,* botanically known as *Petunia×hybrida* and hereinafter referred to by the name 'Fort Salmon 2004'.

The new *Petunia* is a product of a planned breeding program conducted by the Inventor in De Lier, The Netherlands. The objective of the breeding program is to create new freely-branching *Petunia* cultivars with early and freely flowering habit, and unique and attractive flower color.

The new *Petunia* originated from a cross-pollination made by the Inventor in 1999 in De Lier, The Netherlands of two unnamed proprietary selections of *Petunia×hybrida,* not patented. The new *Petunia* was discovered and selected by the Inventor as a single flowering plant within the progeny of the stated cross-pollination in a controlled environment in De Lier, The Netherlands.

Asexual reproduction of the new *Petunia* by terminal cuttings in a controlled environment in De Lier, The Netherlands since 2003, has shown that the unique features of this new *Petunia* are stable and reproduced true to type in successive generations.

SUMMARY OF THE INVENTION

The cultivar Fort Salmon 2004 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fort Salmon 2004'. These characteristics in combination distinguish 'Fort Salmon 2004' as a new and distinct cultivar of *Petunia:*

1. Upright to outwardly spreading growth habit.
2. Freely branching habit.
3. Freely flowering habit.

4. Large salmon pink-colored flowers.
5. Good garden performance.

Plants of the new *Petunia* can be compared to plants of the female parent selection. Plants of the new *Petunia* differ from plants of the female parent selection in the following characteristics:

1. Plants of the new *Petunia* are more outwardly spreading than and not as upright as plants of the female parent selection.
2. Plants of the new *Petunia* are broader than plants of the female parent selection.

Plants of the new *Petunia* can be compared to plants of the male parent selection. Plants of the new *Petunia* differ from plants of the male parent selection in the following characteristics:

1. Plants of the new *Petunia* are broader than plants of the male parent selection.
2. Plants of the new *Petunia* have larger flowers than plants of the male parent selection.

Plants of the new *Petunia* can be compared to plants of the *Petunia* cultivar Fortunia Salmon, not patented. In side-by-side comparisons conducted in De Lier, The Netherlands, plants of the new *Petunia* differed from plants of the cultivar Fortunia Salmon in the following characteristics:

1. Plants of the new *Petunia* were more freely branching than plants of the cultivar Fortunia Salmon.
2. Plants of the new *Petunia* had lighter salmon pink-colored flowers than plants of the cultivar Fortunia Salmon.

BRIEF DESCRIPTION OF THE PHOTOGRAPH

The accompanying colored photograph illustrates the overall appearance of the new *Petunia,* showing the colors as true as it is reasonably possible to obtain in colored reproductions of this type. Colors in the photograph may differ slightly from the color values cited in the detailed botanical description which accurately describe the colors of the new *Petunia.* The photograph comprises a side perspective view of typical flowering plants of 'Fort Salmon 2004' grown in a hanging basket container.

DETAILED BOTANICAL DESCRIPTION

The photograph and following observations, measurements and values describe plants grown in De Lier, The Netherlands, under commercial practice during the late spring and summer in a glass-covered greenhouse with day temperatures averaging 18° C. and night temperatures averaging 18° C. Rooted young plants had been growing for about 13 weeks when the photograph and description were taken. Plants used for the description were grown in 10.5-cm containers. In the following description, color references are made to The Royal Horticultural Society Colour Chart, 1995 Edition, except where general terms of ordinary dictionary significance are used.

Botanical classification: *Petunia×hybrida* cultivar Fort Salmon 2004.

Parentage:

*Female, or seed, parent.*—Unnamed proprietary selection of *Petunia×hybrida,* not patented.

*Male, or pollen, parent.*—Unnamed proprietary selection of *Petunia×hybrida,* not patented.

Propagation:

*Type.*—By terminal cuttings.

*Time to initiate roots, summer.*—About five to seven days at temperatures of 19° C. to 20° C.

*Time to initiate roots, winter.*—About six to eight days at temperatures of 19° C. to 20° C.

*Time to produce a rooted young plant, summer.*—About 14 to 19 days at temperatures of 19° C. to 20° C.

*Time to produce a rooted young plant, winter.*—About two to three weeks at temperatures of 19° C. to 20° C.

*Root description.*—Fine; white in color.

*Rooting habit.*—Freely branching; moderately dense.

Plant description:

*Plant and growth habit.*—Upright to outwardly spreading growth habit; globular in shape. Freely branching habit with about nine primary lateral branches each with multiple secondary lateral branches; pinching is typically not required. Moderately vigorous growth habit.

*Plant height.*—About 14 cm.

*Plant diameter.*—About 26 cm.

Lateral branch description:

*Length.*—About 14 cm.

*Diameter.*—About 2 mm.

*Internode length.*—About 0.5 cm to 1 cm.

*Strength.*—Moderately strong.

*Aspect.*—Initially upright to outwardly spreading.

*Texture.*—Densely pubescent; viscid.

*Color.*—144B.

Foliage description:

*Arrangement.*—Alternate, simple; sessile.

*Length.*—About 4.5 cm.

*Width.*—About 1.9 cm.

*Shape.*—Ovate.

*Apex.*—Acute.

*Base.*—Attenuate.

*Margin.*—Entire.

*Texture, upper and lower surfaces.*—Densely pubescent.

*Venation pattern.*—Pinnate; arcuate.

*Color.*—Developing and fully expanded foliage, upper surface: 137B; venation, 143A to 143B. Developing and fully expanded foliage, lower surface: 138B; venation, 143B to 143C.

Flower description:

*Flower arrangement and habit.*—Relatively large salverform flowers arranged singly arising from leaf axils. Freely flowering habit with usually about ten open flowers and flower buds developing per lateral branch. Flowers not persistent. Flowers face upright to outwardly.

*Fragrance.*—None detected.

*Natural flowering season.*—Plants flower continuously from late spring into autumn in The Netherlands. Plants typically beginning flowering about 6.5 weeks after planting.

*Flower longevity.*—Individual flowers last about five days on the plant.

*Flower diameter.*—About 6.3 cm.

*Flower length (height).*—About 4.5 cm.

*Flower bud.*—Shape: Narrowly oblanceolate. Length: About 2.8 cm. Diameter: About 6 mm. Color: Close to 137B.

*Corolla.*—Arrangement: Five petals fused at the base and opening into a flared trumpet. Petal length from throat: About 5.5 cm. Petal lobe width: About 3.1 cm. Petal shape: Spatulate. Petal apex: Retuse. Petal margin: Entire. Petal texture, upper and lower surfaces: Smooth, glabrous; satiny. Throat texture: Smooth, glabrous. Tube texture: Densely pubescent. Color: Petal, when opening, upper surface: 54A. Petal, when opening, lower surface: 55C. Petal, fully opened, upper surface: 55A to 55B; color becoming closer to 55B with development. Petal, fully opened, lower surface: 55C.

*Calyx.*—Arrangement: One star-shaped calyx tube with five sepals fused at the base per flower. Sepal length: About 1.8 cm. Sepal width: About 3 mm. Sepal shape: Narrowly oblong. Sepal apex: Acute. Sepal margin: Entire. Sepal texture, upper and lower surfaces: Densely pubescent. Color, immature and mature, upper surface: 137D. Color, immature and mature, lower surface: 137B.

*Peduncles.*—Length: About 3.4 cm. Diameter: About 2 mm. Angle: Erect to about 40° from stem axis. Strength: Moderately strong. Texture: Densely pubescent; viscid. Color: 144A.

*Reproductive organs.*—Stamens: Quantity/arrangement: Five per flower. Filament length: About 2.4 cm. Anther shape: Broadly reniform. Anther length: About 2.3 mm. Anther color: 158C. Pollen amount: Moderate. Pollen color: 155A. Pistils: Quantity: One per flower. Pistil length: About 2.5 cm. Style length: About 2.2 cm. Style color: 143C. Stigma shape: Flattened, three-lobed. Stigma color: 145C. Ovary color: 143C to 143D. Seed/fruit: Seed and fruit development have not been observed on plants of the new *Petunia.*

Garden performance: Plants of the new *Petunia* have been observed to have good garden performance and tolerate wind, rain and temperatures ranging from about 5° C. to about 35° C.

Pathogen/pest resistance: Plants of the new *Petunia* have not been observed to be resistant to pathogens and pests common to *Petunia.*

It is claimed:

1. A new and distinct *Petunia* plant named 'Fort Salmon 2004' as illustrated and described.

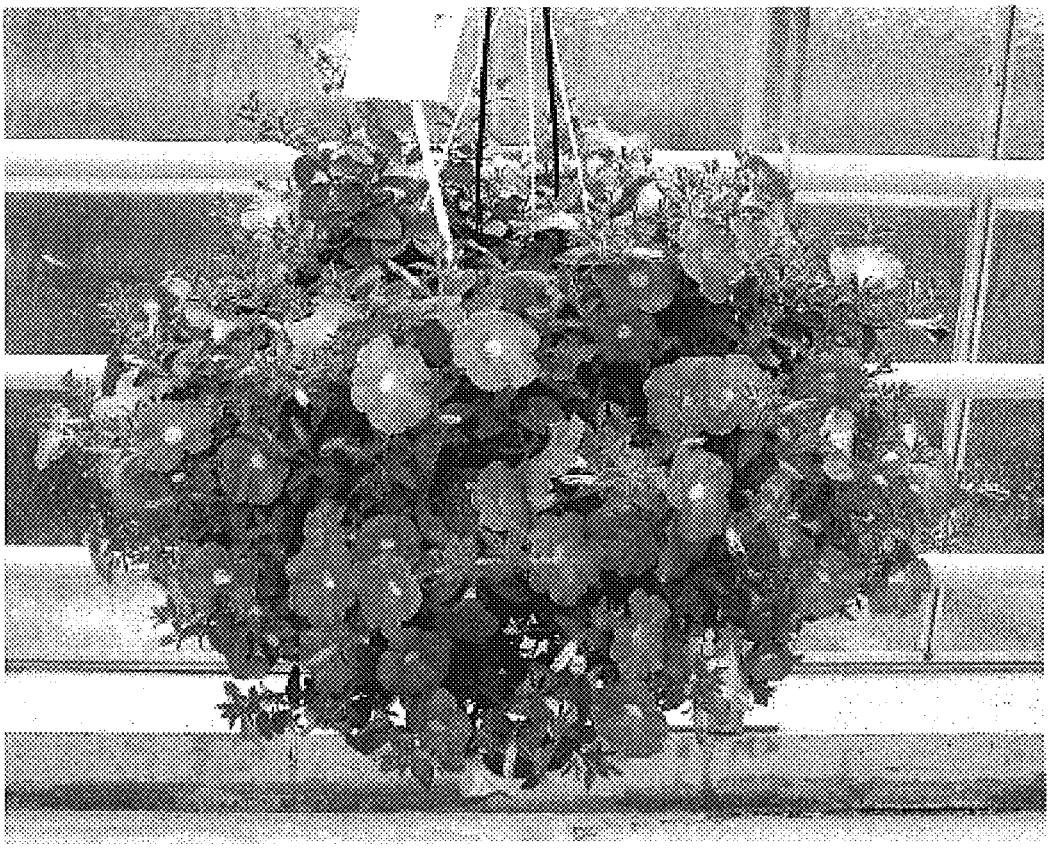

* * * * *